US012735671B2

(12) United States Patent
Lee et al.

(10) Patent No.: US 12,735,671 B2
(45) Date of Patent: Sep. 15, 2026

(54) METHOD FOR MECHANICALLY SEPARATING TISSUE AND CELLS CONSTITUTING BIOLOGICAL TISSUE

(71) Applicant: Jun Seok Lee, Busan (KR)

(72) Inventors: Jun Seok Lee, Busan (KR); Hasim Eray Copcu, Izmir (TR)

(73) Assignee: Jun Seok Lee, Busan (KR)

(*) Notice: Subject to any disclaimer, the term of this patent is extended or adjusted under 35 U.S.C. 154(b) by 414 days.

(21) Appl. No.: 17/914,769

(22) PCT Filed: Mar. 12, 2021

(86) PCT No.: PCT/KR2021/003108
§ 371 (c)(1),
(2) Date: Sep. 27, 2022

(87) PCT Pub. No.: WO2021/194143
PCT Pub. Date: Sep. 30, 2021

(65) Prior Publication Data

US 2023/0105704 A1 Apr. 6, 2023

(30) Foreign Application Priority Data

Mar. 27, 2020 (KR) ........................ 10-2020-0037420
Mar. 2, 2021 (KR) ........................ 10-2021-0027205

(51) Int. Cl.
*C12M 1/33* (2006.01)
*C12M 1/00* (2006.01)

(52) U.S. Cl.
CPC ............ *C12M 45/02* (2013.01); *C12M 45/06* (2013.01)

(58) Field of Classification Search
CPC ..... C12M 45/02; C12M 45/06; C12N 5/0667; C12N 2509/10
See application file for complete search history.

(56) References Cited

U.S. PATENT DOCUMENTS 5,690,825 A 11/1997 Parton
6,358,474 B1 * 3/2002 Dobler .................... G01N 1/34 435/270

(Continued)

FOREIGN PATENT DOCUMENTS

DE 102007041049 3/2008
JP 2012080821 4/2012

(Continued)

OTHER PUBLICATIONS

Biachi et al., A New Nonenzymatic Method and Device to Obtain a Fat Tissue Derivative Highly Enriched in Pericyte-Like Elements by Mild Mechanical Forces from Human Lipoaspirates, 2013, Cell Transplantation, vol. 22, pp. 2063-2077. (Year: 2013).*

*Primary Examiner* — Kathryn Elizabeth Limbaugh
(74) *Attorney, Agent, or Firm* — JCIPRNET

(57) ABSTRACT

The present invention relates to a method for mechanically separating tissue and cells, and more specifically, to a method for mechanically separating tissue and cells, the method comprising the steps of: preparing adipose tissue; diluting the adipose tissue with a diluent to prepare an adipose tissue mixed solution; micronizing the adipose tissue, and various tissue and cells constituting the adipose tissue, in the adipose tissue mixed solution; and separating the adipose tissue and the various tissue and cells constituting the adipose tissue, in the adipose tissue mixed solution.

10 Claims, 4 Drawing Sheets

(56) References Cited

U.S. PATENT DOCUMENTS

| | | | |
|---|---|---|---|
| 2018/0155691 A1* | 6/2018 | Shani | B01L 3/502 |
| 2019/0017012 A1 | 1/2019 | Banju et al. | |

FOREIGN PATENT DOCUMENTS

| | | |
|---|---|---|
| JP | 3218433 | 10/2018 |
| JP | 2019033691 | 3/2019 |
| KR | 100821128 | 4/2008 |
| KR | 20140038354 | 3/2014 |
| KR | 20160119609 | 10/2016 |
| KR | 1020170093105 | 8/2017 |
| KR | 20190026586 | 3/2019 |
| KR | 1020190026586 | 3/2019 |
| WO | 2010045389 | 4/2010 |

* cited by examiner

METHOD FOR MECHANICALLY SEPARATING TISSUE AND CELLS CONSTITUTING BIOLOGICAL TISSUE

TECHNICAL FIELD

The following description relates to a method of mechanically separating various tissue and cells constituting biological tissue.

BACKGROUND ART

Biological tissue includes various tissue, cells, and materials that may be used for regenerative treatment and cosmetic purposes, and various methods for separating the tissue, cells, and materials have been used. In particular, for adipose tissue, a method of disintegrating and centrifuging tissue using an enzyme has been widely used generally, but since there is no suitable medical enzyme and the enzyme to be used is toxic, there is a controversy about the safety of materials obtained from the adipose tissue decomposed using the enzyme. Accordingly, there are various attempts to obtain materials that may be used for regenerative treatment and cosmetic purposes from the adipose tissue without using the enzyme. For example, US Patent Publication Document discloses filtration method and apparatus.

DISCLOSURE OF THE INVENTION

Technical Goals

An aspect provides a method for mechanically separating tissue and cells capable of improving separation process efficiency of tissue and cells useful in biological tissue, particularly adipose tissue, and stromal cells, that is, cells containing adipose tissue-derived stem cells by physical, chemical and electro-mechanical effects of dilution by performing a pretreatment process such as dilution before a micronizing process of biological tissue.

However, technical objects of the present disclosure are not limited to the aforementioned purpose and other objects which are not mentioned may be clearly understood by those skilled in the art from the following description.

Technical Solutions

According to an aspect, there is provided a method for mechanically separating tissue and cells including steps of: preparing adipose tissue; diluting the adipose tissue with a diluent to prepare an adipose tissue mixed solution; micronizing the adipose tissue, and various tissue and cells constituting the adipose tissue, in the adipose tissue mixed solution; and separating the adipose tissue and the various tissue and cells constituting the adipose tissue, in the micronized adipose tissue mixed solution.

In an example embodiment, the diluent may include at least one selected from the group consisting of buffered saline, a dextrose solution, a maltodextrin solution, ethanol, physiological saline, a lactate Ringer's solution, a Ringer's solution, a balanced electrolyte solution, platelet-rich plasma (PRP), platelet-poor plasma (PPP), a mixed solution of PRP and PPP, and an intravenous injection solution.

In an example embodiment, a dilution ratio of the adipose tissue to the diluent in the adipose tissue mixed solution may be 1:99 to 99:1 (v/v).

In an example embodiment, the diluent may be 25% (volume) to 75% (volume) of the adipose tissue mixed solution.

In an example embodiment, the preparing of the adipose tissue mixed solution may be adjusting the number of cells and cell density per unit volume of the tissue and cells recovered according to the dilution ratio of the diluent.

In an example embodiment, the micronizing of the adipose tissue and the various tissue and cells constituting the adipose tissue may be performed by using at least one process of cutting, tearing, scraping, disintegration and separation.

In an example embodiment, the micronizing of the adipose tissue and the various tissue and cells constituting the adipose tissue may be micronizing the adipose tissue to sizes of 10 μm to 4,000 μm.

In an example embodiment, the micronizing of the adipose tissue and the various tissue and cells constituting the adipose tissue may be moving the adipose tissue mixed solution through a plurality of screen through holes sequentially, back and forth repeatedly, or both.

In an example embodiment, the plurality of screens may include through holes having different sizes or the same size, and the plurality of screens may include through holes having different shapes or the same shape.

In an example embodiment, each of the plurality of screens may include a through hole having a size of 10 μm to 4,000 μm.

In an example embodiment, the plurality of screens may be arranged sequentially according to a size of the through hole, and include sharp edges protruding from the surface, inside, or both of the through hole.

In an example embodiment, the micronizing of the adipose tissue and the various tissue and cells constituting the adipose tissue may be performed by using an apparatus including a housing mounting a plurality of screens having a plurality of through holes with different sizes therein and connectors connecting a syringe to both surfaces of the housing.

In an example embodiment, the separating of the adipose tissue and the various tissue and cells constituting the adipose tissue, in the micronized adipose tissue mixed solution may be separating the adipose tissue according to a size and a specific gravity using at least one of centrifugation, vibration, and filtering.

In an example embodiment, the separating of the adipose tissue and the various tissue and cells constituting the adipose tissue, in the micronized adipose tissue mixed solution may be separating stromal cells including tissue and stem cells constituting the adipose tissue.

Effects

According to the present disclosure, it is possible to perform a diluting process of diluting adipose tissue with a physiological saline, a lactate Ringer's solution, a Ringer's solution, a balanced electrolyte solution, a platelet-rich plasma (PRP), a platelet-poor plasma (PPP), a mixed solution of PRP and PPP, or solutions that can be administered by intravenous injection before performing a mechanical micronizing process in a process of mechanically separating various tissue and cells constituting adipose tissue, to separate various cells constituting more adipose tissue and cells containing rich adipose tissue-derived stromal cells, that is, stem cells by physical, chemical and electro-mechanical effects of dilution by the pre-diluting method, and to improve separation process efficiency.

BEST MODE FOR CARRYING OUT THE INVENTION

Figure 1:
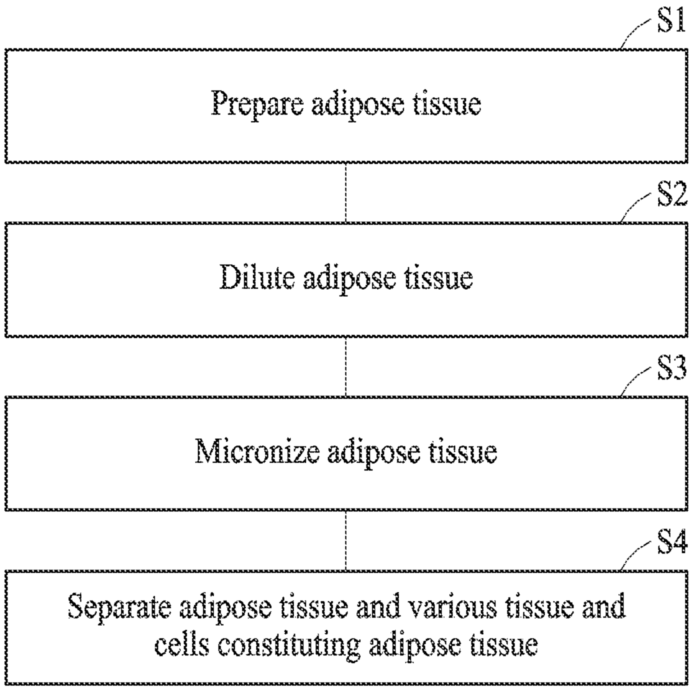
FIG. 1 is an exemplary view illustrating a process flowchart of a separation method according to an example embodiment of the present disclosure.

Hereinafter, example embodiments of the present disclosure will be described in detail with reference to the accompanying drawings. In describing the example embodiment of the present disclosure, a detailed description of known functions or constitutions will be omitted if it is determined that they unnecessarily make the gist of the present disclosure unclear. Terminologies used herein are terminologies used to properly express example embodiments of the present disclosure, which may vary according to a user, an operator's intention, or customs in the art to which the present disclosure pertains. Accordingly, definitions of the terminologies need to be described based on contents throughout this specification. Like reference numerals illustrated in the respective drawings designate like members.

Throughout this specification, it will be understood that when a member is referred to as being "on" another member, it can be directly on the other member or intervening members may also be present.

Throughout the specification, when a certain part "comprises" a certain component, it will be understood to imply the inclusion of stated elements but not the exclusion of any other elements.

Hereinafter, a method for mechanically separating tissue and cells of the present disclosure will be described in detail with reference to example embodiments and drawings. However, the present disclosure is not limited to these example embodiments and drawings.

The present disclosure relates to a method for mechanically separating various tissue and cells constituting tissue, and according to an example embodiment of the present disclosure, the separating method may include step S1 of preparing adipose tissue; step S2 of diluting the adipose tissue; step S3 of micronizing the adipose tissue; and step S4 of separating the adipose tissue and the various tissue and cells constituting the adipose tissue.

According to an example embodiment of the present disclosure, step S4 of preparing the adipose tissue may be a step of preparing an adipose tissue sample for separating tissue and cells constituting adipose tissue by including stem cells from the adipose tissue, and may collect adipose tissue derived from an animal (fish, mammal, etc.) and the like and prepare concentrated adipose tissue that may be used for separating tissue and cells constituting the adipose tissue. For example, in order to collect the adipose tissue by a desired method such as liposuction, excision of the adipose tissue, and the like and concentrate a lipoaspirate or the adipose tissue, impurities located in a top layer (oil) and a lower layer of the adipose tissue separated by decanting or centrifugation may be removed. The decanting may correspond to a method for separating moisture or blood under the adipose tissue when the adipose tissue floats after a few minutes when a suction container still stands because the adipose tissue is lighter than blood or water.

According to an example embodiment of the present disclosure, step S2 of diluting the adipose tissue may be a step of diluting the adipose tissue with a diluent to prepare an adipose tissue mixed solution, and may perform a diluting process depending on various protocols/methods according to an amount and a density of a tissue and cells mixed solution to finally recover (or separate) the concentrated adipose tissue before processing, that is, mechanically processing such as a micronizing process and a separation process of the adipose tissue. For example, according to a dilution ratio of the diluent, it is possible to adjust the cell number and the cell density per unit volume of the adipose tissue used for the separation process or the tissue and cells mixed solution finally recovered, and to increase a separated amount of various tissue, cells and stromal cells constituting the adipose tissue.

According to an example embodiment of the present disclosure, the diluent may be a solution that may be applied to an intravenous route, and may include at least one selected from the group consisting of a buffered saline, a dextrose solution, a maltodextrin solution, ethanol, saline, a ringer lactate, a ringer, a balanced electrolyte or solution, a platelet-rich plasma (PRP), a platelet-poor plasma (PPP), a mixed solution of PRP and PPP, and an intravenous injection solution. That is, in the process of mechanically separating and obtaining various tissue and cells constituting the adipose tissue from the adipose tissue, the predilution of diluting the adipose tissue using a physiological saline, a ringer lactate, a ringer, a balanced electrolyte solution, a platelet-rich plasma (PRP), a platelet-poor plasma (PPP), or a mixture or solution of PRP and PPP which may be applied by any intravenous injection route may increase the separation of the adipose tissue and various tissue and cells constituting the adipose tissue due to physical, chemical and/or electromechanical effects upon dilution and improve the efficiency of the process of separating various tissue and cells constituting the adipose tissue.

In an example embodiment of the present disclosure, the diluent may have a dilution ratio of the adipose tissue to the diluent in the adipose tissue mixed solution of 1:99 to 99:1 (v/v); 20:80 to 80:20 (v/v); or 50:50 to 20:80 (v/v), and preferably, the diluent may be 25% (volume) to 75% (volume) in the adipose tissue mixed solution. The dilution may be appropriately adjusted according to the volume of an apparatus and a system used in the micronizing process and the separating process, and the number of cells and/or the cell density included in the dilution of the recovered cells and tissue may be adjusted. For example, dilution is performed before mechanical treatment by using a 50% diluent and 50% adipose tissue, such as any intravenous injection solution, and the next process may be performed. More specifically, 5 cc of adipose tissue and 5 cc of a diluent are used in a 10 cc syringe or container, or 10 cc of adipose tissue and 10 cc of a dilution may be used in a 20 cc syringe or container.

According to an example embodiment of the present disclosure, step S3 of micronizing the adipose tissue may be a step of micronizing adipose tissue and various tissue and cells constituting the adipose tissue in the diluted adipose tissue mixed solution, and the adipose tissue may be micronized using at least one process of cutting, tearing, scraping, disintegration, and separation.

As an example of the present disclosure, step S3 of micronizing the adipose tissue may be micronizing adipose tissue, adipocytes, stromal cells including stem cells, biomaterials, and the like uniformly to a size of 10 μm to 4,000 μm, in the adipose tissue mixed solution.

According to an example embodiment of the present disclosure, step S3 of micronizing the adipose tissue may be micronizing the adipose tissue mixed solution using a system or apparatus having a plurality of screens.

For example, the plurality of screens may include through holes of different sizes or the same size, and may include through holes of different shapes or the same shape. Accordingly, it is possible to improve the efficiency of the separation process by micronizing various sizes of adipocytes and stromal cells.

For example, the plurality of screens may include a single through hole or a plurality of through holes, respectively.

For example, the plurality of screens may include through holes each having a size of 10 μm to 4,000 μm, and the through holes may include at least one of a spherical shape, an elliptical shape, a polygonal shape, and a grid shape. The size may mean a diameter, a length, or the like of the through hole.

Figure 4:
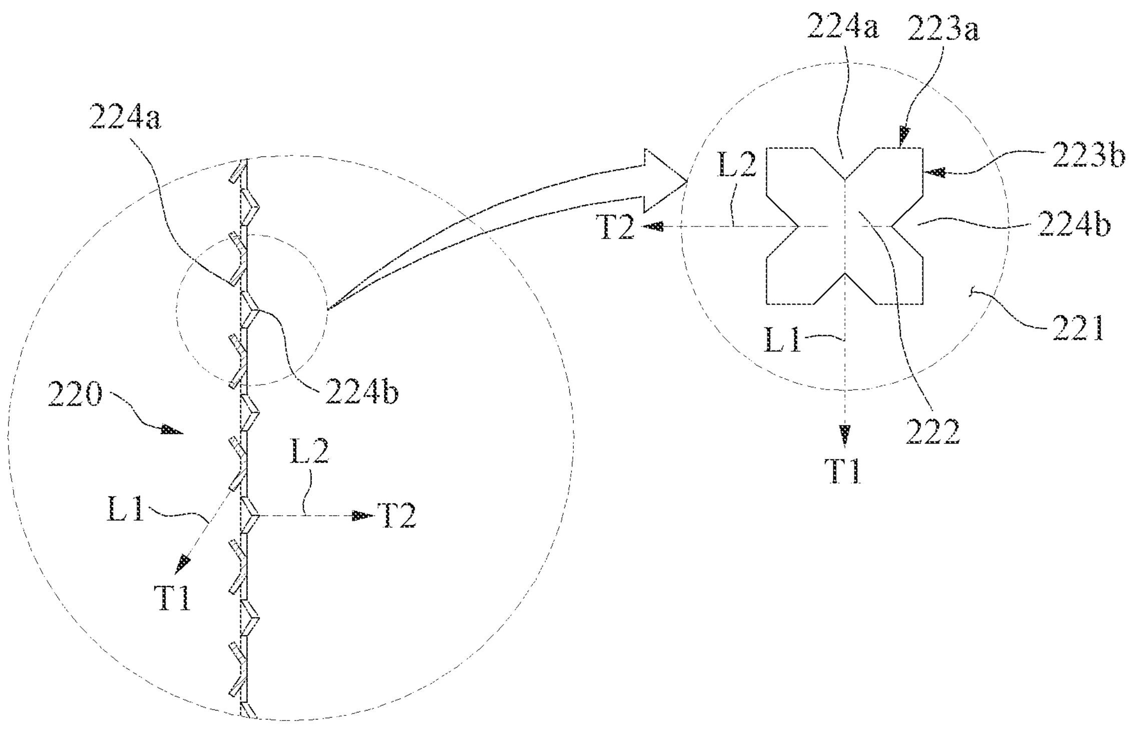
FIG. 4 is a diagram exemplarily illustrating a screen of an apparatus used in the method of the present disclosure according to an example embodiment of the present disclosure.

For example, the through hole includes a sharp edge protruding from the surface, inside, or both of the through hole may be included, and as illustrated in FIG. 4, may protrude in the form of a blade including a sharp edge.

For example, the plurality of screens may be sequentially arranged according to the size of the through hole in the system or apparatus, and may be arranged in order of larger sizes or smaller sizes of through holes.

For example, the adipose tissue mixed solution is introduced into the system or the apparatus in which the plurality of screens is arranged, moves from an inlet to an outlet, and may be micronized while passing through the through holes of the plurality of screens sequentially, iteratively back and forth, or both.

For example, the number of repetitions of moving adipose tissue to pass through the through holes in the system or apparatus in which the plurality of screens is arranged may be about 3 to 30 times. For example, the moving may be repeated from a screen with large micropores to a screen with relatively small pores or vice versa.

As an example of the present disclosure, the apparatus provided with the plurality of screens in which the micronizing process is performed to obtain tissues and cells constituting adipose tissue from diluted adipose tissue may use a biological tissue micronizing system 1 illustrated in FIG. 1. The biological tissue micronizing system 1 may include a first syringe C1, a second syringe C2, a second cover 160, a first cover 150, a housing 110, a second locker 192, and a first locker 191. The biological tissue micronizing system 1 includes the first syringe C1 and the second syringe C2 which are mounted between both connectors in the housing 110 in which a disk 120 including the plurality of screens with various sizes of through holes having protrusions in the form of a blade with a sharp blade is mounted and connected to the connectors at both sides of the housing 110, respectively. The first syringe C1 and the second syringe C2 may include a first container and a second container configured to receive a diluted adipose tissue mixture BT, respectively, and a first push rod configured to apply pressure therein and press the adipose tissue BT toward the screen 120. When the diluted adipose tissue repeatedly moves via the housing 110 to pass through the screen by pressing plungers of the two syringes C1 and C2, respectively, homogeneous micronized adipose tissue of various sizes may be obtained and homogenized microfat of various sizes and other tissue and cells constituting the adipose tissue may be mechanically separated using the obtained micronized adipose tissue.

For example, the plurality of screens has through holes having sizes of 10 μm to 4000 μm and includes through holes in a shape of which edges in the form of a blade protrude toward the center of the through holes, and may be arranged in order of screens having microholes having sizes of 2000 μm to 3000 μm, 1000 μm to 2000 μm, 500 μm to 1000 μm, and 250 μm to 500 μm.

For example, in the plurality of screens, the disk 120 including the plurality of screens in the micronizing system 1 may include a plate 121 and a plurality of screens 122*a*, 122*b*, 122*c*, 122*d*, and 122*e*. The plate 121 may be fixed to a first mount 111. The plate 121 may include a first central opening 1211. That is, the plate 121 may be configured to select a first screen 122*a* among the plurality of screens 122*a*, 122*b*, 122*c*, 122*d*, and 122*e* including the plurality of through holes configured to micronize the adipose tissue and micronize the adipose tissue with the selected first screen 122*a*, and then select a second screen 122*b* among the plurality of screens 122*a*, 122*b*, 122*c*, 122*d*, and 122*e* and micronize the adipose tissue with the selected second screen 122*b*. Here, the selection and order of the plurality of screens 122*a*, 122*b*, 122*c*, 122*d*, and 122*e* are determined by a user and thus are not restricted to the selection and order of the screens described above.

Referring to FIG. 4, the configuration of the screen is exemplarily shown in the apparatus provided with the plurality of screens according to an example embodiment of the present disclosure, and in FIG. 4, the screen 220 may include a plate 221 and a through hole 222. The through hole 222 may be defined by a plurality of edges of the plate 221. For example, the screen 220 may include a first linear portion 223*a* formed on a first side of the through hole 222, a first protrusion 224*a* formed on the first side of the through hole 222 and protruding in a first direction T1 toward the center of the through hole 222, a second linear portion 223*b* formed on a second side of the through hole 222, and a second protrusion 224*b* formed on the second side of the through hole 222 and protruding in a second direction T2 toward the center of the through hole 222. The first protrusion 224*a* and the second protrusion 224*b* may be oriented at an angle with respect to the screen 220, and may be configured to scrape and tear the adipose tissue passing through the screen 220. A first extension line L1 of the first protrusion 224*a* protruding in the first direction T1 and a second extension line L2 of the second protrusion 224*b* protruding in the second direction T2 may be twisted to each other. That is, the first extension line L1 and the second extension line L2 may not be parallel to each other and may not meet each other. The first protrusion 224*a* and the second protrusion 224*b* may have the direction T1 of the first protrusion 224*a* and the second direction T2 of the second protrusion 224*b* set to face any one cover of the first cover 150 and the second cover 160.

According to an example embodiment of the present disclosure, step S4 of separating the adipose tissue and the various tissue and cells constituting the adipose tissue may be a step of separating microfat and various tissue and cells constituting the adipose tissue in the adipose tissue mixed solution and may be performed using centrifugation, decanting, vibration, filtering, and the like.

As an example of the present disclosure, desired adipose tissue and cells may be separated according to a specific gravity and/or size using at least one of centrifugation, vibration, and filtering. As an example, after the separating process of the adipose tissue mixed solution is subjected to the micronizing process by centrifugation, when the adipose tissue mixed solution is separated into four layers (a triglyceride layer; adipose tissue, a stromal cell aggregate layer in which cells are aggregated to a boundary layer between the adipose tissue and a diluent+a body fluid; and a stromal cell solution layer containing the diluent, the body fluid, and the stem cells), among them, i) a stromal cell solution layer having the stem cells at the bottom layer and a layer in which the cells immediately thereon are aggregated may be recovered from a syringe. The two layers may be mixed with each other to be prepared for application (treatment). ii) When only a solution is desired, a lowest solution layer called a stem cell or stromal cell solution (diluent+body fluid+stromal cells) layer may be used. iii) When only the final product in the form of a gel is desired, the cell aggregate layer, which is the second layer from the lowest layer (stromal cell solution layer), may be recovered and this layer may be used as a gel because of its high viscosity. Alternatively, this layer may be directly mixed and used with normal adipose tissue. Alternatively, after this layer is obtained, this layer may be used after being diluted with a desired diluent.

As another example, as a triglyceride layer which is a top layer is removed from the final product, upper adipose tissue may be mixed with a lower entire stromal differentiation layer, that is, a stromal cell aggregate layer, which refers to all layers below the adipose tissue layer, and a stromal cell solution layer containing a diluent, a body fluid and stromal cells. The mixture may be used as a cell-enriched adipose tissue graft.

Hereinafter, the present disclosure will be described in more detail with reference to the following Examples, but the following Examples are only for illustrative purposes and are not intended to limit the scope of the present disclosure.

EXAMPLES

Figure 2:
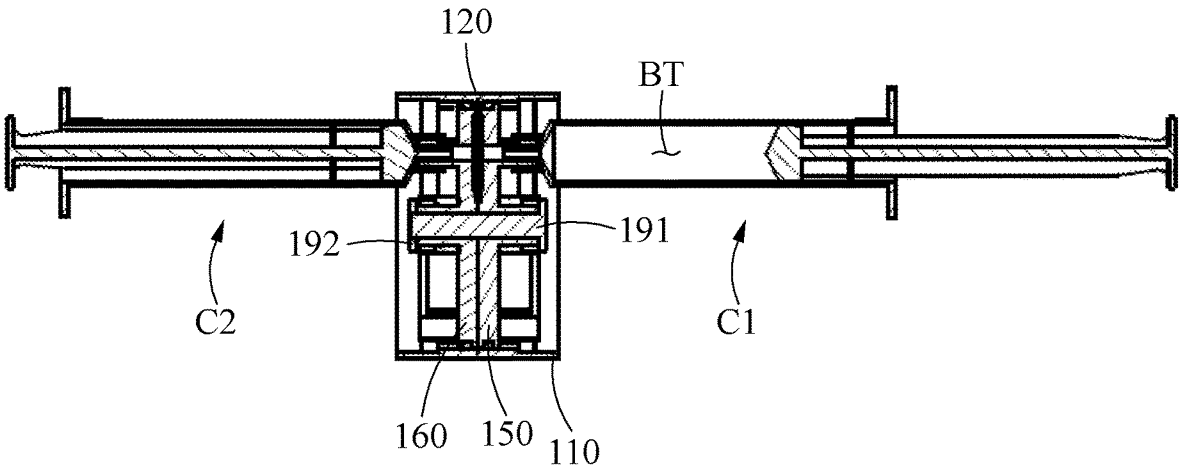
FIG. 2 is a front sectional view illustrating an apparatus used in the method of the present disclosure, according to an example embodiment of the present disclosure.
Figure 3:
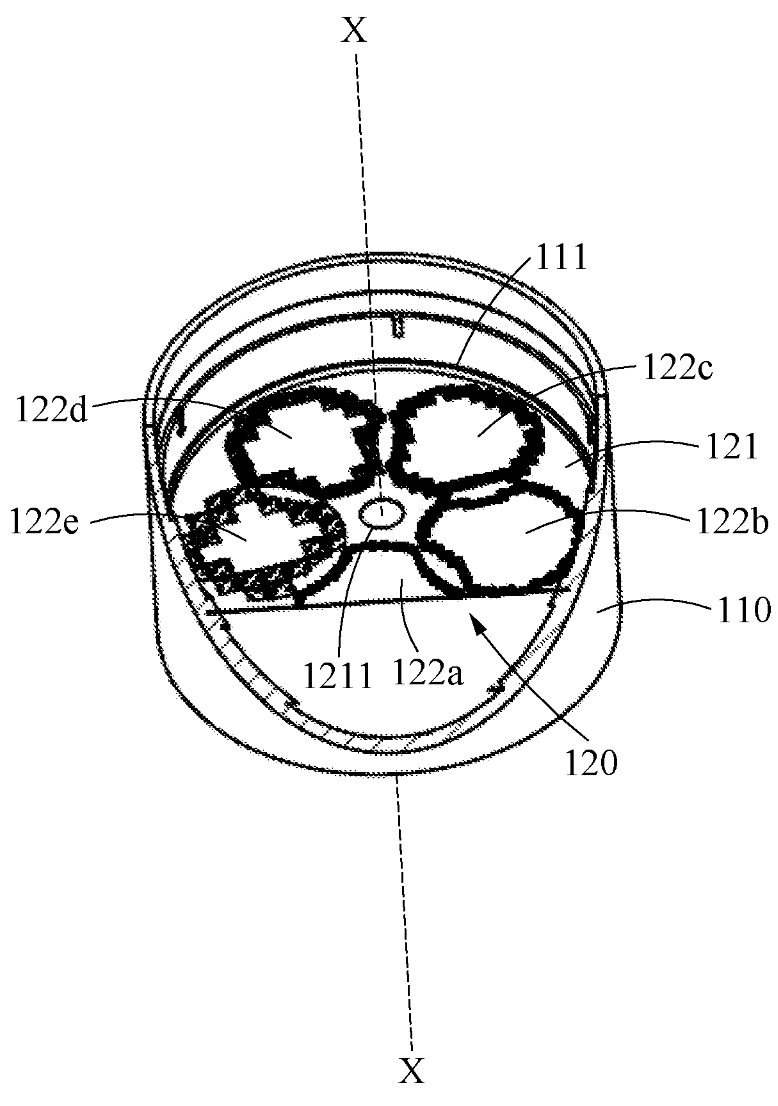
FIG. 3 is a cutout perspective view exemplarily illustrating a partial structure of the device of FIG. 2 according to an example embodiment of the present disclosure.

Impurities were removed from adipose tissue collected by liposuction from the human body and after centrifugation, concentrated adipose tissue was prepared. The concentrated adipose tissue was subjected to a dilution process according to Tables 1 and 2 and repeatedly micronized 30 times using a plurality of screens having through holes having sizes of 400 μm to 4,000 μm in an apparatus of FIG. 2. Before the micronizing process, the number and density of stromal cells (nucleated cells) were analyzed according to a dilution process and a dilution ratio, and are shown in Tables 1 and 2. A ratio of the number of nucleated cells to a control group in which the dilution process was not performed before the micronizing process is shown.

Referring to Tables 1 and 2, it can be seen that when diluting before the micronizing process using the diluent, the number and density of stromal cells (nucleated cells) may be increased, and the amount of stromal cells (nucleated cells) separated from adipose tissue through the mechanical separation process may be increased.

TABLE 1

Different Ratios of Pre-micronizing Dilutions

| Total Volume: 10 ml | Nucleated cells/ml | Total stromal-cells volume (ml) | Total Nucleated cell number | Nucleated cells in 1 mL condensed fat | Compare with control |
|---|---|---|---|---|---|
| Control (No dilution) | 1,500,000 | 2 | 3,000,000 | 300,000 | |
| Example 1 (diluent: NaCl 0.9%) | | | | | |
| 25% | 1,120,000 | 3 | 3,360,000 | 448,000 | 149% |
| 50% | 852,000 | 5 | 4,260,000 | 852,000 | 284% |
| 75% | 270,000 | 6 | 1,620,000 | 648,000 | 216% |
| Example 2 (diluent: Ringer) | | | | | |
| 25% | 1,300,000 | 3 | 3,900,000 | 520,000 | 173% |
| 50% | 900,000 | 5 | 4,500,000 | 900,000 | 300% |
| 75% | 300,000 | 6 | 1,800,000 | 720,000 | 240% |
| Example 3 (diluent: Plasma (PPP)) | | | | | |
| 25% | 2,600,000 | 4 | 10,400,000 | 1,386,667 | 462% |
| 50% | 2,440,000 | 5.5 | 13,420,000 | 2,684,000 | 895% |
| 75% | 780,000 | 7 | 5,460,000 | 2,184,000 | 728% |

TABLE 2

Different Ratios of Pre-micronizing Dilutions

| Total Volume: 20 ml | Nucleated cells/mL | Total stromal-cells volume (ml) | Total Nucleated cell number | Nucleated cells in 1 mL condensed fat | Compare with control |
|---|---|---|---|---|---|
| Control (No dilution) | 1,350,000 | 4.5 | 6,075,000 | 303,750 | |
| Example 4 (diluent: NaCl 09%) | | | | | |
| 25% | 1,080,000 | 6 | 6,480,000 | 432,000 | 142% |
| 50% | 750,000 | 11 | 8,250,000 | 825,000 | 272% |
| 75% | 200,000 | 14 | 2,800,000 | 560,000 | 184% |

TABLE 2-continued

Different Ratios of Pre-micronizing Dilutions

| Total Volume: 20 ml | Nucleated cells/mL | Total stromal-cells volume (ml) | Total Nucleated cell number | Nucleated cells in 1 mL condensed fat | Compare with control |
|---|---|---|---|---|---|
| Example 5 (diluent: Ringer) | | | | | |
| 25% | 1,100,000 | 6 | 6,600,000 | 440,000 | 145% |
| 50% | 800,000 | 11 | 8,800,000 | 880,000 | 290% |
| 75% | 210,000 | 14 | 2,940,000 | 588,000 | 194% |
| Example 6 (diluent: Plasma (PPP)) | | | | | |
| 25% | 2,600,000 | 8 | 20,800,000 | 1,386,667 | 457% |
| 50% | 1,900,000 | 13 | 24,700,000 | 2,470,000 | 813% |
| 75% | 680,000 | 14 | 9,520,000 | 1,904,000 | 627% |

As described above, although the example embodiments have been described by the restricted example embodiments and the drawings, various modifications and variations can be made from the above description by those skilled in the art. For example, even if the described techniques are performed in a different order from the described method, and/or components described above are coupled or combined in a different form from the described method, or replaced or substituted by other components or equivalents, an appropriate result can be achieved. Therefore, other implementations, other example embodiments, and equivalents to the appended claims fall within the scope of the claims to be described below.

The invention claimed is:

1. A method for mechanically separating tissue and cells, the method comprising steps of:

preparing adipose tissue;

diluting the adipose tissue with a diluent to prepare an adipose tissue mixed solution, wherein the preparing of the adipose tissue mixed solution includes adjusting the number of cells and cell density per unit volume of the tissue and cells recovered according to a dilution ratio of the diluent;

micronizing the adipose tissue, and tissue and cells constituting the adipose tissue, in the adipose tissue mixed solution; and separating the adipose tissue and the tissue and cells constituting the adipose tissue, in the micronized adipose tissue mixed solution, wherein the micronizing of the adipose tissue and the tissue and cells constituting the adipose tissue includes moving the adipose tissue mixed solution through a plurality of screen through holes back and forth repeatedly, wherein a plurality of screens comprise sharp edges formed by a plurality of protrusions protruding toward a center of the plurality of screen through holes, and wherein the micronizing the adipose tissue, and tissue and cells constituting the adipose tissue includes micronizing to a size of 10 μm to 4,000 μm performed by tearing the adipose tissue as the adipose tissue mixed solution moves back and forth through the sharp edges.

2. The method of claim 1, wherein the diluent includes at least one selected from the group consisting of buffered saline, a dextrose solution, a maltodextrin solution, ethanol, physiological saline, a lactate Ringer's solution, a Ringer's solution, a balanced electrolyte solution, platelet-rich plasma (PRP), platelet-poor plasma (PPP), a mixed solution of PRP and PPP, and an intravenous injection solution.

3. The method of claim 1, wherein a dilution ratio of the adipose tissue to the diluent in the adipose tissue mixed solution is 1:99 to 99:1 (v/v).

4. The method of claim 1, wherein the diluent is 25% (volume) to 75% (volume) of the adipose tissue mixed solution.

5. The method of claim 1, wherein the plurality of screens includes through holes having different sizes or the same size, and the plurality of screens includes through holes having different shapes or the same shape.

6. The method of claim 1, wherein each of the plurality of screens includes a through hole having a size of 10 μm to 4,000 μm.

7. The method of claim 1, wherein the plurality of screens is arranged sequentially according to a size of the plurality of screen through holes.

8. The method of claim 1, wherein the micronizing of the adipose tissue and the tissue and cells constituting the adipose tissue is performed by using an apparatus including a housing mounting the plurality of screens having the plurality of screen through holes with different sizes therein and connectors connecting a syringe to both opposite surfaces of the housing.

9. The method of claim 1, wherein the separating of the adipose tissue and the tissue and cells constituting the adipose tissue, in the micronized adipose tissue mixed solution is separating the adipose tissue according to a size and a specific gravity using at least one of centrifugation, vibration, and filtering.

10. The method of claim 1, wherein the separating of the adipose tissue and the tissue and cells constituting the adipose tissue, in the micronized adipose tissue mixed solution is separating stromal cells including tissue and stem cells constituting the adipose tissue.

* * * * *